(12) United States Patent
Cathey, Jr.

(10) Patent No.: US 6,536,898 B1
(45) Date of Patent: Mar. 25, 2003

(54) EXTENDED DEPTH OF FIELD OPTICS FOR HUMAN VISION

(75) Inventor: Wade Thomas Cathey, Jr., Boulder, CO (US)

(73) Assignee: The Regents of the University of Colorado, Boulder, CO (US)

(*) Notice: Subject to any disclaimer, the term of this patent is extended or adjusted under 35 U.S.C. 154(b) by 0 days.

(21) Appl. No.: 09/663,883

(22) Filed: Sep. 15, 2000

(51) Int. Cl.[7] ................................................. G02C 7/04
(52) U.S. Cl. .......................... 351/160 R; 623/6.17; 359/558
(58) Field of Search ......................... 351/160 R, 160 H, 351/161–162; 359/558–559, 563–564; 623/6.11, 6.17; 356/124.5; 382/254–255

(56) References Cited

U.S. PATENT DOCUMENTS 5,476,515 A * 12/1995 Kelman et al. ............ 623/6.59
5,748,371 A * 5/1998 Cathey, Jr. et al. ......... 369/558

OTHER PUBLICATIONS

Optics by Eugene Hecht Second Edition pp. 177–181; 1987.*

* cited by examiner

Primary Examiner—Jordan M. Schwartz
(74) Attorney, Agent, or Firm—Curtis A. Vock; Lathrop & Gage L.C.

(57) ABSTRACT

The present invention provides extended depth of focus (EDF) to human eyes by modifying contact lenses, interocular implants, or the surface of the eye itself. This is accomplished by applying selected phase variations to the optical element in question (for example, by varying surface thickness). The phase variations EDF-code the wavefront and cause the optical transfer function to remain essentially constant within some range away from the in-focus position. This provides a coded image on the retina. The human brain decodes this coded image, resulting in an in-focus image over an increased depth of focus.

13 Claims, 5 Drawing Sheets

EXTENDED DEPTH OF FIELD OPTICS FOR HUMAN VISION

CROSS-REFERENCE TO RELATED APPLICATIONS

U.S. Pat. No. 5,748,371, issued May 5, 1998 and entitled "Extended Depth of Field Optical Systems," is incorporated herein by reference.

BACKGROUND OF THE INVENTION

1. Field of the Invention

This invention relates to apparatus and methods for increasing the depth of field and decreasing the wavelength sensitivity of incoherent optical systems. In particular, this invention relates to extended depth of focus optics for human vision.

2. Description of the Prior Art

In the human eye, it is well known that the accommodation of the lens decreases with age, and the bifocal or trifocal glasses are eventually needed in many cases. When a human lens must be replaced, an intraocular implant is usually designed for viewing objects at infinity, and the person then uses reading glasses and other glasses of various strengths for vision at closer distances.

Current techniques that are used experimentally in intraocular implants provide two or more foci, for reading and distance vision, for example. This is done either with a shorter focal length lens placed in the center of a lens of a longer focal length, for example, or by use of diffractive optics that provides two foci. The result is one in-focus image and one out-of-focus image. The human brain disregards the out-of-focus image and concentrates on the in-focus image. The major disadvantage of this technique is that if the two images are not aligned (as occurs when the lens is not centered, a frequent occurrence with contact lenses) the images do not line up and the out-of-focus image is apparent. As such a two-foci contact lens moves, the images move with respect to each other. Another disadvantage is loss of contrast. That is, the image looks washed out. The situation is even worse when the object is located between a reading distance and a very long distance; examples include the distance to a computer screen, a television set, or music on a stand. In these cases, two poorly focussed images are superimposed.

Another commonly used approach is called monovision: a person is fitted with a lens on one eye for reading, and another lens on the other eye for distance viewing. The brain then selects the best focussed image to concentrate on. Again, images of objects that are at an intermediate distance cannot be seen clearly. Otherwise, this approach works for many people, but the inability to fuse images that are not both focussed has made this solution unusable for many others. In that case, the user sees two misregistered images.

The human brain can adapt to unchanging visual conditions, even when they markedly affect the immediate visual perception. An example of this was discussed above, where the brain is able to adapt to two images if one is in focus, by concentrating on the in-focus image and ignoring the other.

As another example, the human brain can accommodate for the very large distortions present in varifocal lenses, which gradually move from providing clear vision at a distance, for objects seen through the upper portion of the lens, to providing clear vision of close objects when seen through the lower inside part of the lenses. Objects at an intermediate distance can be seen through the center of the lenses.

An extreme example of how the brain can adapt to unchanging conditions was shown in experiments where mirrors were used to invert the images seen by a person. After a day or so, the brain turned the images upside down, so that the person saw a normal image.

The human brain cannot adjust to conventional out-of-focus images, because the amount of blur changes with misfocus, or with distance from the in-focus plane. In addition, the blur is such that some information about the object being seen is lost.

There is a need to extend the depth of focus of the human eye by modifying contact lenses, intraocular implants, and the surface of the eye itself (with laser surgery, for example).

SUMMARY OF THE INVENTION

An object of the present invention is to provide extended depth of focus (EDF) by modifying contact lenses, intraocular implants, and natural human eyes. This is accomplished by applying selected phase variations to the optical elements in question (for example, by varying surface thickness). These phase variations EDF-code the wavefront and cause the optical transfer function to remain essentially constant within a large range away from the in-focus position. The human brain undoes the EDF-coding effects, resulting in an in-focus image over an increased depth of focus. While the human brain cannot compensate for general out-of-focus images, where the amount of blur changes with distance from the in-focus plane, it can compensate for the specific EDF-coding misfocus added by the optical mask, because that misfocus does not change with distance, and the phase variations are selected so that no information is lost in the process.

For cases where the person still has some refocussing capability, the eye will change focus such that the image of the object being viewed falls into the extended region where the brain can decode the image. In the case of an, intraocular implant to replace a damaged lens, the amount of wavefront coding is tailored to give the required amount of invariance in the point spread function. The depth of focus can be increased to be 800% or greater than that of the normal eye.

The selected phase variations to be applied to the optical element (for example, by varying surface thickness) are asymmetric phase distributions that modify the point spread function of the imaging system so that it does not change over a very large distance. There are a variety of wavefront coding shapes that can be used, including cubic phase functions.

DETAILED DESCRIPTION OF THE PREFERRED EMBODIMENTS

Figure 1:
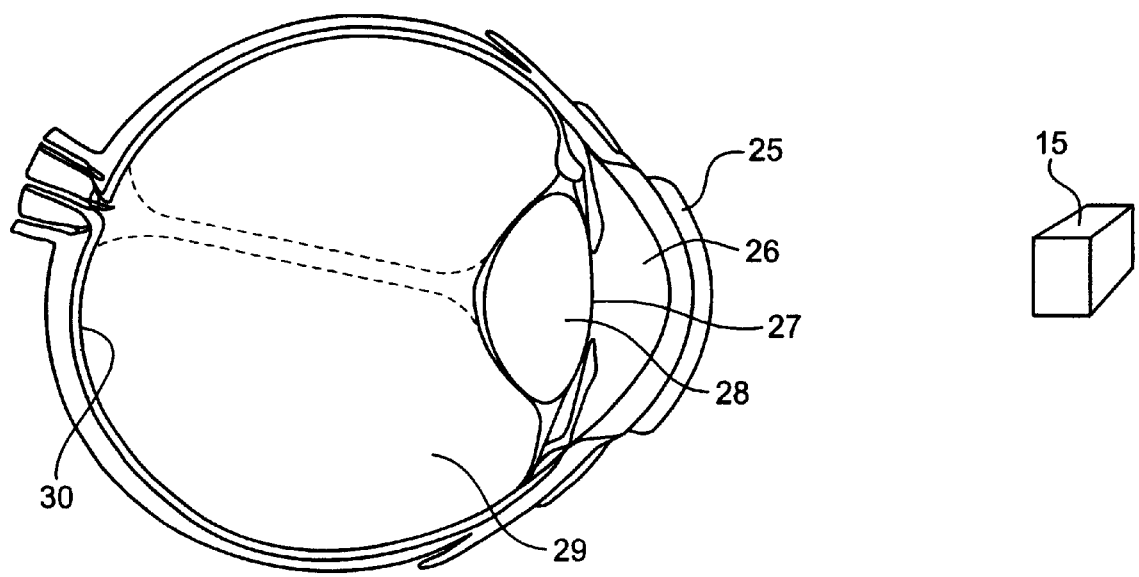
FIG. 1 (prior art) shows a standard prior art imaging system using a contact lens.

FIG. 1 (prior art) shows a conventional optical imaging system using a contact lens over an eye. Object 15 is imaged through contact lens 25, through the cornea 26, the iris 27, lens 28, and the vitreous humor 29 onto the retina 30. Such a system creates a sharp, in-focus image at the retina 30 only if object 15 is located at or very close to the in-focus object plane. Some accommodation is provided by the lens 28. However, this lens hardens with age and loses its ability to refocus. If the distance from the back principal plane of lens 28 to retina 30 is $d_i$, and the focal length of contact lens 25 is f, the distance from the front principal plane of lens 28 to object 15, $d_0$ must be chosen such that:

$$1/d_0 + 1/d_i - 1/f = 0$$

in order for the image at retina 30 to be in adequate focus. The depth of field of an optical system is the distance that the object can move away from the in-focus distance and still have the image be in focus. For a simple system like FIG. 1, the depth of focus is very small, unless the light is bright and the iris is stopped down.

Prior attempts to solve this problem have used contact lenses and optical implants that have multiple (usually two) foci. One focus is correct for objects at infinity, and one is correct for objects at a close distance. This means that two images of an object at one of those locations are formed, one in focus, and one out of focus.

Figure 2:
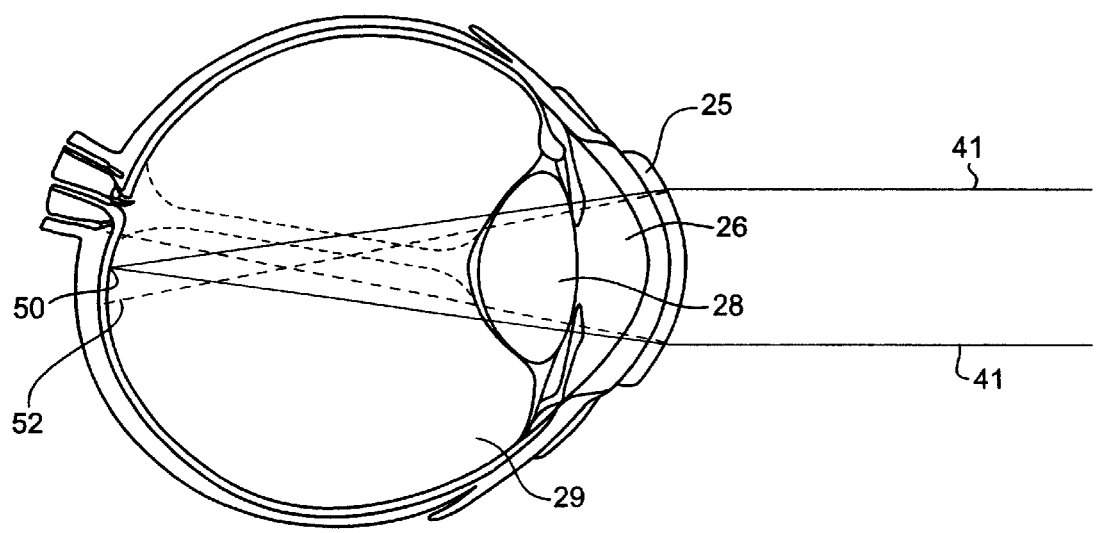
FIG. 2 shows how two images are formed in a standard prior art imaging system.

FIG. 2 shows this effect when imaging a point at infinity. Rays 41 form a point image 50 at one of the foci of the combined system formed by contact lens, 25, cornea 26, and lens 28. The second focus of the system forms a blurred image 52. When the point object is at a reading distance, the previously blurred image 52 is in focus, and the image 50 becomes blurred. At other distances, neither image is in focus, and the degree of misfocus changes with object location.

A general form of one family of EDF-coding phase variations is:

$$P(x,y) = \exp(j((\alpha x^3 + \beta y^3 + \gamma x^2 y + \delta xy^2)), \ x^2 + y^2 \leq 1$$

Choice of the constants, α, β, γ, and δ allow phase functions that are rectangularly separable (with γ=δ=0) to systems whose modulation transfer functions (MTF's) are circularly symmetric (α=β=$\alpha_0$, γ=δ=−3$\alpha_0$). For simplicity we will use the symmetric rectangularly separable form, which is given by:

$$P(x,y) = \exp(j\alpha(x^3 + y^3)), \ x^2 + y^2 \leq 1$$

where α is a parameter used to adjust the depth of field increase.

Since this form is rectangularly separable, for most analyses its one-dimensional component can be considered:

$$p(x,y) = \exp(j\alpha x^3), \ x^2 \leq 1$$

As the absolute value of α increases, the depth of field increases. The image contrast before post-processing also decreases as α increases. This is because as α increases, the MTF slumps down.

Figure 3:
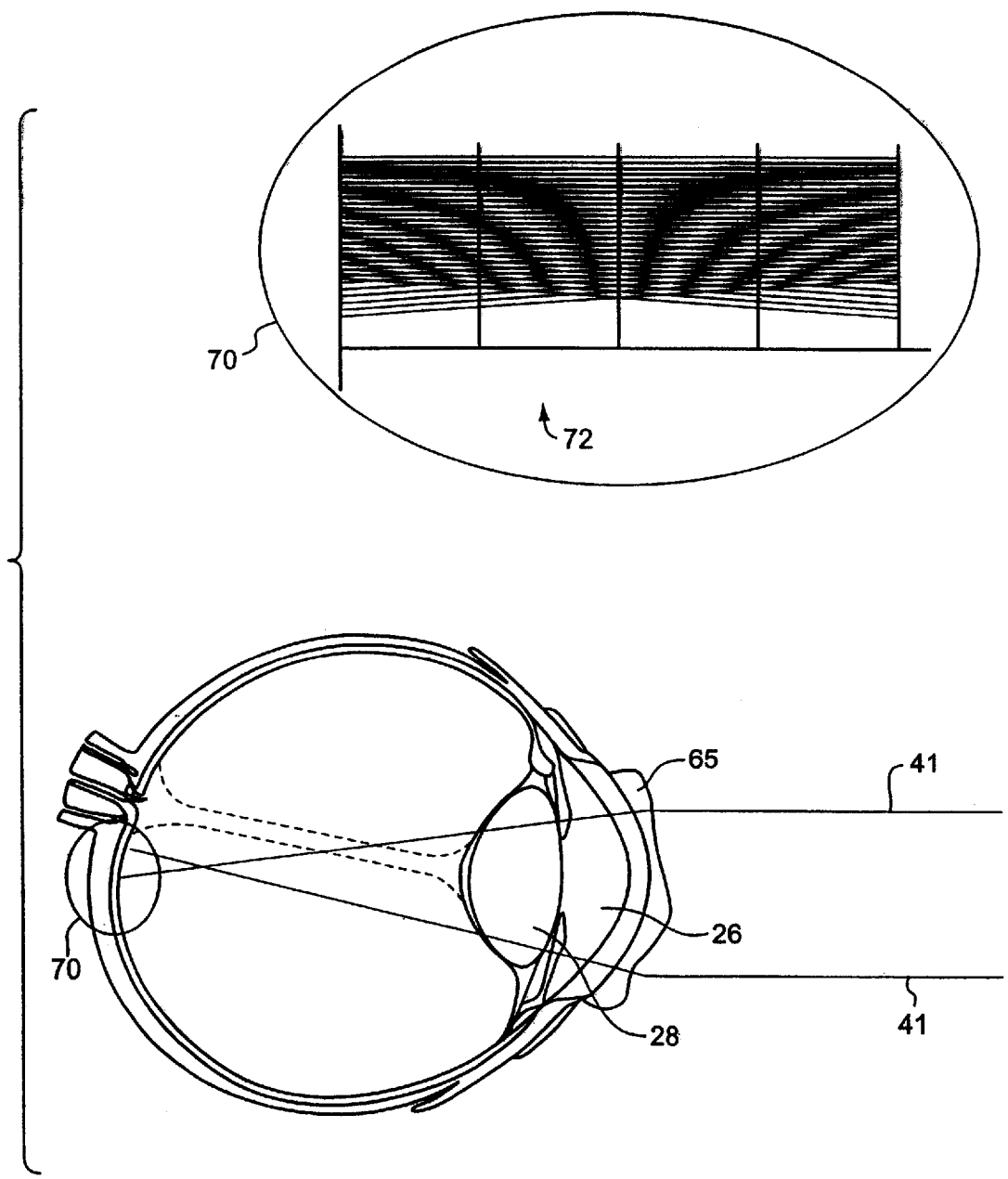
FIG. 3 shows an Extended Depth of Field (EDF) contact lens imaging system in accordance with the present invention.

FIG. 3 shows the effect of the EDF-coding phase element on the rays that pass through the eye. Rays 41, which come from a point at infinity, pass through contact lens 65, cornea 26, and lens 28, do not form a focus anywhere. Phase coding might be applied by variations in the thickness of lens 65 (exaggerated here for clarity).

An expanded view of the ray pattern near the retina 30 is shown in expanded view 70 where the retina is at plane 72. This is unlike the ray pattern for an eye with a normal contact lens, It also is unlike the two-foci lens of FIG. 2. As the object point moves in from infinity, the ray pattern in the region of the retina, shown expanded in 70, moves to the left, but the cross section of the ray pattern that falls on the retina does not change appreciably. This means that no matter where the object is, the same pattern will fall on the retina. When the object is not a point, the object distribution is convolved with the unchanging ray distribution (the point spread function). The brain can deconvolve the resulting coded image because the point spread function of the eye, modified with the EDF-coding optics, does not change appreciably. This is in contrast to the changes that normally occur in the point spread function when there is misfocus.

For large enough α, the MTF of a system using a cubic PM mask can be approximated by:

$$|H|(u, \Psi) \approx \sqrt{\frac{\pi}{3|\alpha u|}}, \ u \neq 0$$

$$|H|(u, \Psi) \approx 2, \ u = 0$$

Where u is the spatial frequency in the x direction and Ψ is the degree of misfocus. Thus, the cubic-PM mask is an example of a mask which modifies the optical system to have a near-constant MTF over a range of object distances. The particular range for which the MTF does not vary much is dependent on α. This range (and thus the depth of field) increases with α. However, the amount that the depth of field can be increased is practically limited by the fact that contrast decreases as α increases. However, for the human eye only moderate increases in depth of field are needed.

Figure 4:
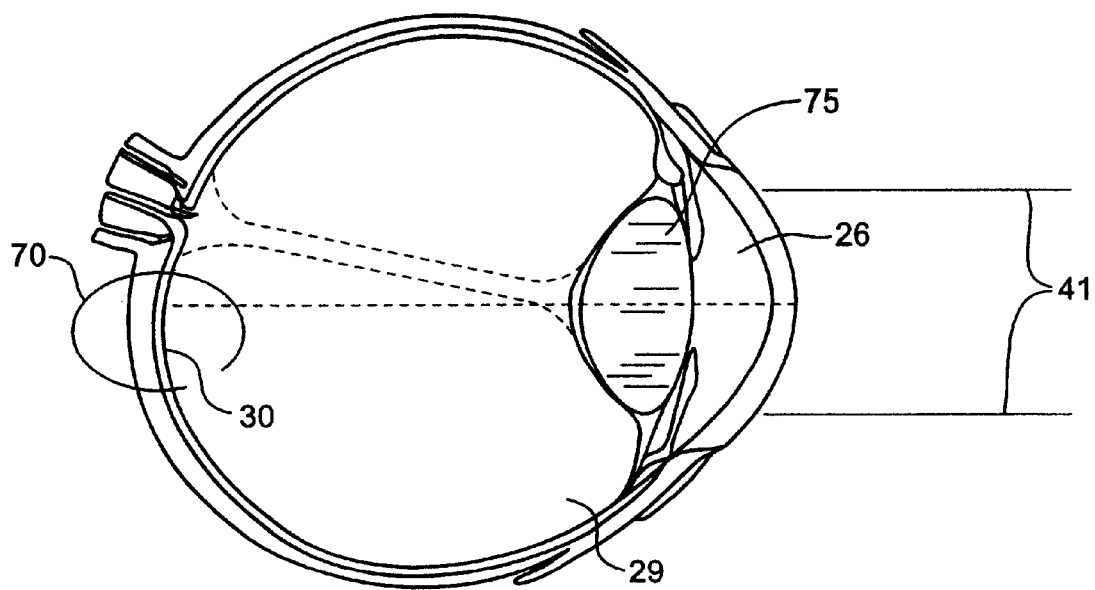
FIG. 4 shows an Extended Depth of Field (EDF), intraocular implant imaging system in accordance with the present invention.

FIG. 4 shows an Extended Depth of Field (EDF) intraocular implant imaging system in accordance with the present invention where the EDF-coding optical shape is on the implant lens 75. The phase coding results in misfocus as shown in expanded view 70 of FIG. 3.

Figure 5:
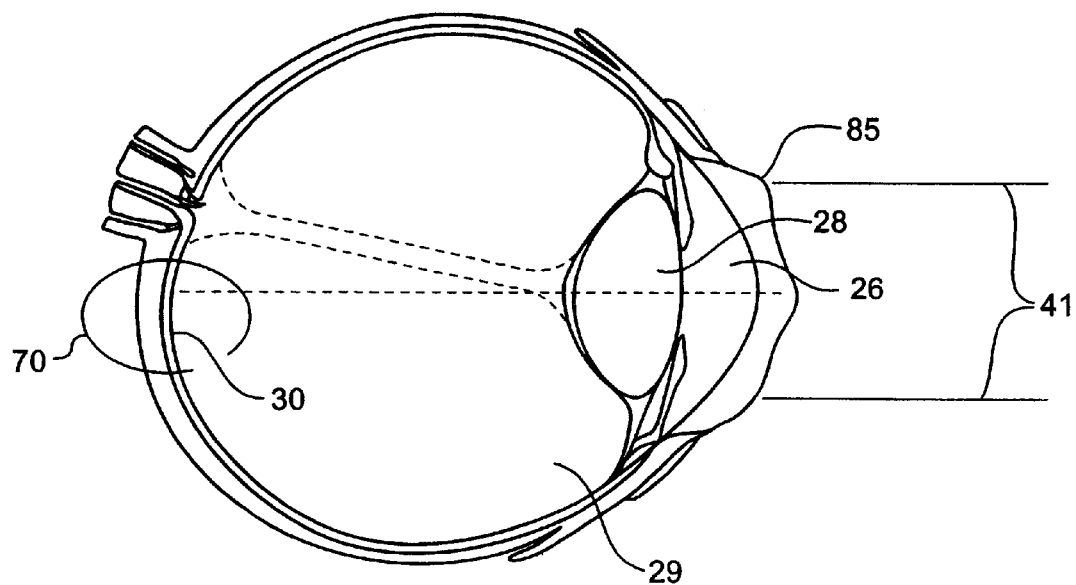
FIG. 5 shows an Extended Depth of Field (EDF) modified natural eye imaging system in accordance with the present invention.
Figure 1:
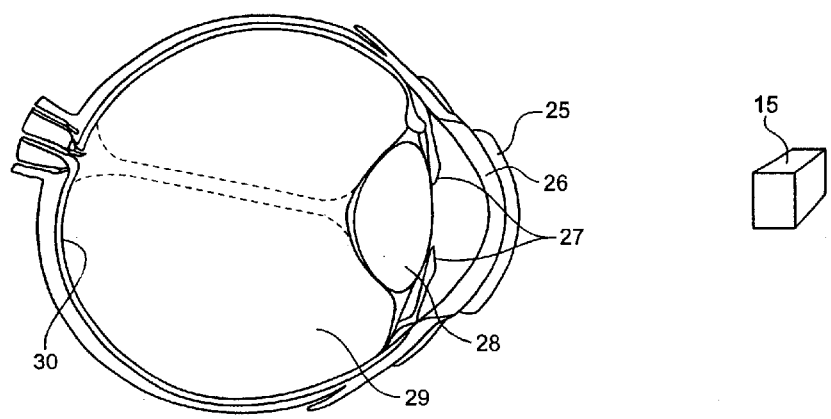
Figure 2:
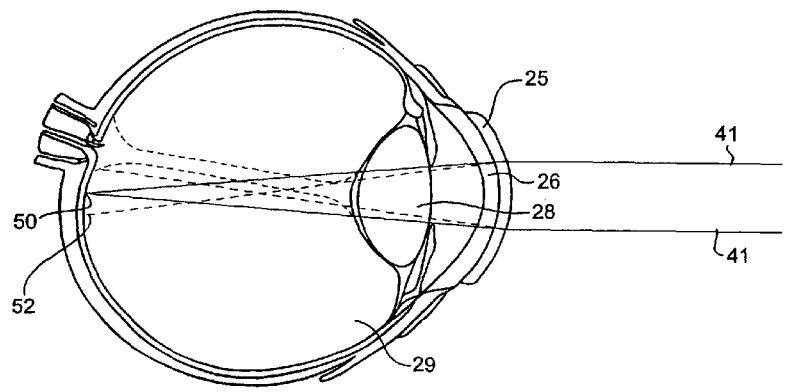
Figure 3:
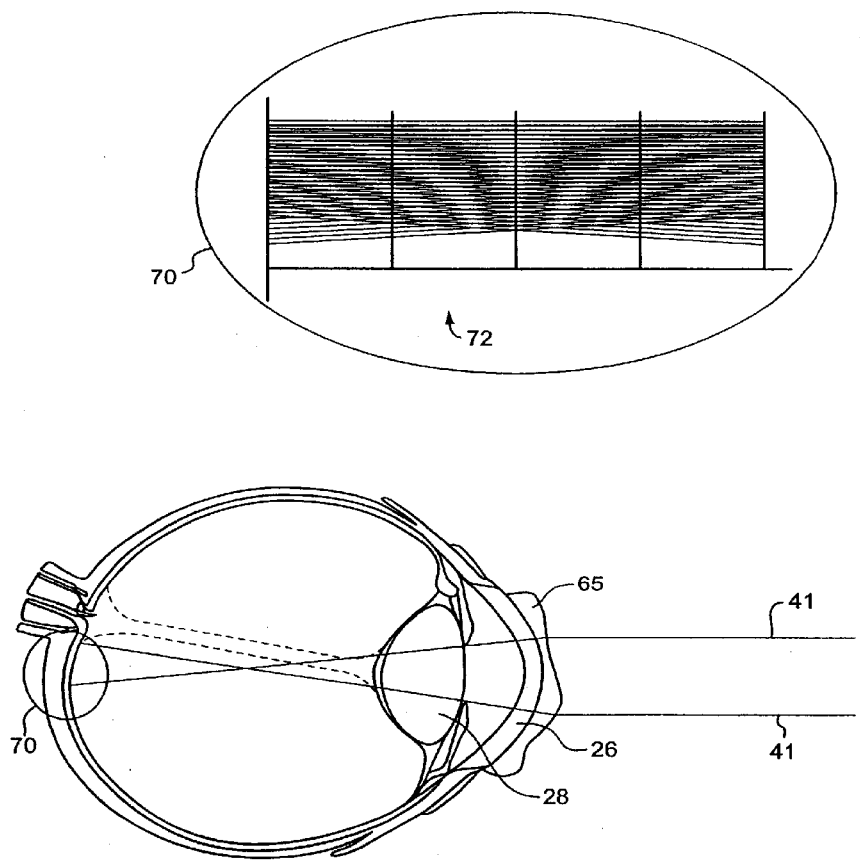
Figure 4:
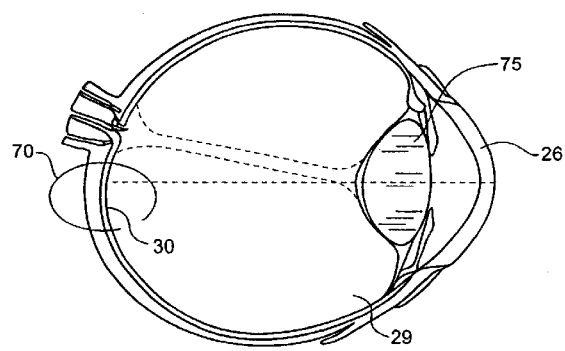
Figure 5:
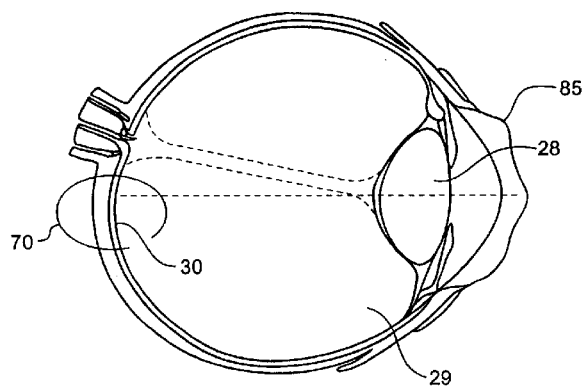

FIG. 5 shows an Extended Depth of Field (EDF) modified natural eye imaging system in accordance with the present invention where the EDF-coding optical shape is on the cornea 85. The cornea can be modified using laser surgery, e.g. Phase coding is applied by variations in the thickness of cornea 85 (exaggerated here for clarity). The phase coding results in misfocus as shown in expanded view 70 of FIG. 3.

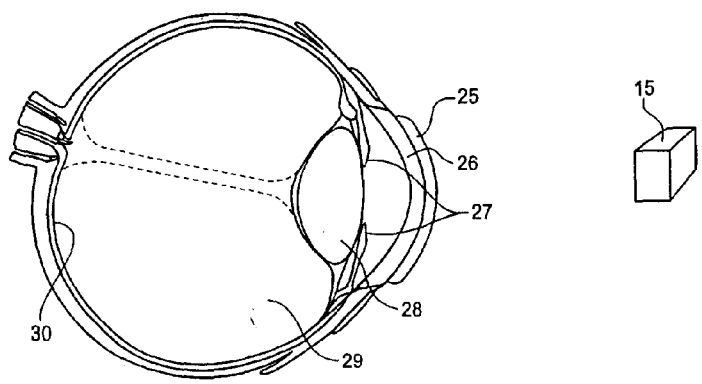

What is claimed is:

1. Apparatus for increasing the depth of field of an optical system comprising:

an optical mask positioned between the object and the eye retina, said mask being constructed and arranged to alter the optical transfer function of the optical system in such a way that the altered optical transfer function is substantially insensitive to the distance between the object and the optical system over a greater range of object distances than was provided by the unaltered optical transfer function, wherein said mask affects said alteration to the optical transfer function substantially by affecting the phase of light transmitted by said mask, and wherein said optical system is structured such that a brain connected with the eye retina decodes the altered optical transfer function to benefit by the increased depth of field.

2. Apparatus for increasing the depth of field of an optical system comprising: a contact lens having an optical mask positioned between the object and the eye retina, the mask being constructed and arranged to alter the optical transfer function of the optical system in such a way that the altered optical transfer function is substantially insensitive to the distance between the object and the optical system over a greater range of object distances than was provided by the unaltered optical transfer function, wherein the mask affects the alteration to the optical transfer function substantially by affecting the phase of light transmitted by the mask.

3. Apparatus for increasing the depth of field of an optical system comprising: an intraocular implant having an optical mask positioned between the object and the eye retina, the mask being constructed and arranged to alter the optical transfer function of the optical system in such a way that the altered optical transfer function is substantially insensitive to the distance between the object and the optical system over a greater range of object distances than was provided by the unaltered optical transfer function, wherein the mask affects the alteration to the optical transfer function substantially by affecting the phase of light transmitted by the mask.

4. Apparatus for increasing the depth of field of an optical system comprising: a variation on a surface of a cornea forming an optical mask positioned between the object and the eye retina, the mask being constructed and arranged to alter the optical transfer function of the optical system in such a way that the altered optical transfer function is substantially insensitive to the distance between the object and the optical system over a greater range of object distances than was provided by the unaltered optical transfer function, wherein the mask affects the alteration to the optical transfer function substantially by affecting the phase of light transmitted by the mask.

5. The method for increasing the depth of field in a human vision system comprising the steps of:

altering the optical transfer function of an optical system between the object to be viewed and the human retina in such a way that the altered optical transfer function is substantially insensitive to the distance between the object and the optical system over a greater range of object distances than was provided by the unaltered optical transfer function, wherein said alteration step accomplishes said alteration of the optical transfer function substantially by affecting the phase of light transmitted through the optical system, and structuring the optical system such that the altered optical transfer function is decoded with a brain connected with the eye retina.

6. A contact lens for increasing the depth of field of human vision, comprising: an optical mask constructed and arranged to alter the optical transfer function of an eye when positioned on the eye between an object and a retina of the eye such that the altered optical transfer function is substantially insensitive to the distance between the object and the eye over a greater range of object distances than was provided by the unaltered optical transfer function, wherein the optical mask affects the alteration to the optical transfer function substantially by affecting the phase of light transmitted by the optical mask.

7. An intraocular implant for increasing the depth of field of human vision, comprising: an optical mask constructed and arranged to alter the optical transfer function of an eye when positioned in the eye between an object and a retina of the eye such that the altered optical transfer function is substantially insensitive to the distance between the object and the eye over a greater range of object distances than was provided by the unaltered optical transfer function, wherein the optical mask affects the alteration to the optical transfer function substantially by affecting the phase of light transmitted by the optical mask.

8. Optics for increasing the depth of field of human vision, comprising: an optical mask constructed and arranged as an alteration of a corneal surface of an eye to alter the optical transfer function of the eye such that the altered optical transfer function is substantially insensitive to the distance between the object and the eye over a greater range of object distances than was provided by the unaltered optical transfer function, wherein the optical mask affects the alteration to the optical transfer function substantially by affecting the phase of light transmitted by the optical mask.

9. A method for increasing the depth of field of human vision, comprising the steps of:

altering the optical transfer function of an eye imaging an object to a retina of the eye such that the altered optical transfer function is substantially insensitive to the distance between the object and the eye over a greater range of object distances than was provided by the unaltered optical transfer function, wherein the step of altering alters the optical transfer function substantially by affecting the phase of light transmitted through the eye.

10. A method of claim 9, further comprising the step of decoding the altered optical transfer function with a brain connected with the eye to benefit by the increased depth of field.

11. A method of claim 9, the step of altering comprising utilizing a contact lens positioned on the eye, the contact lens being modified to form an optical mask for affecting the phase of light transmitted through the eye.

12. A method of claim 9, the step of altering comprising utilizing an intraocular implant positioned within the eye, the intraocular implant being modified to form an optical mask for affecting the phase of light transmitted through the eye.

13. A method of claim 9, the step of altering comprising altering a surface of a cornea of the eye to form an optical mask for affecting the phase of light transmitted through the eye.

* * * * *

UNITED STATES PATENT AND TRADEMARK OFFICE
CERTIFICATE OF CORRECTION

PATENT NO.    : 6,536,898 B1
DATED         : March 25, 2003
INVENTOR(S)   : Wade Thomas Cathey, Jr.

It is certified that error appears in the above-identified patent and that said Letters Patent is hereby corrected as shown below:

The Title page, showing an Illustrative figure, should be deleted and substitute therefore the attached title page.

Delete drawing sheet(s) 1-5, and substitute therefore the drawing sheet(s) consisting of Fig(s) 1-5 as shown on the attached pages.

Signed and Sealed this

Twelfth Day of August, 2003

JAMES E. ROGAN
*Director of the United States Patent and Trademark Office*

(12) United States Patent
Cathey, Jr.

(10) Patent No.: US 6,536,898 B1
(45) Date of Patent: Mar. 25, 2003

(54) EXTENDED DEPTH OF FIELD OPTICS FOR HUMAN VISION

(75) Inventor: Wade Thomas Cathey, Jr., Boulder, CO (US)

(73) Assignee: The Regents of the University of Colorado, Boulder, CO (US)

(*) Notice: Subject to any disclaimer, the term of this patent is extended or adjusted under 35 U.S.C. 154(b) by 0 days.

(21) Appl. No.: 09/663,883

(22) Filed: Sep. 15, 2000

(51) Int. Cl.$^7$ .............................................. G02C 7/04
(52) U.S. Cl. ............................... 351/160 R; 623/6.17; 359/558
(58) Field of Search ....................... 351/160 R, 160 H, 351/161–162; 359/558–559, 563–564; 623/6.11, 6.17; 356/124.5; 382/254–255

(56) References Cited

U.S. PATENT DOCUMENTS 5,476,515 A * 12/1995 Kelman et al. ............ 623/6.59
5,748,371 A * 5/1998 Cathey, Jr. et al. ......... 369/558

OTHER PUBLICATIONS

Optics by Eugene Hecht Second Edition pp. 177–181; 1987.*

* cited by examiner

*Primary Examiner*—Jordan M. Schwartz
(74) *Attorney, Agent, or Firm*—Curtis A. Vock; Lathrop & Gage L.C.

(57) ABSTRACT

The present invention provides extended depth of focus (EDF) to human eyes by modifying contact lenses, interocular implants, or the surface of the eye itself. This is accomplished by applying selected phase variations to the optical element in question (for example, by varying surface thickness). The phase variations EDF-code the wavefront and cause the optical transfer function to remain essentially constant within some range away from the in-focus position. This provides a coded image on the retina. The human brain decodes this coded image, resulting in an in-focus image over an increased depth of focus.

13 Claims, 5 Drawing Sheets